United States Patent [19]

Brunel et al.

[11] Patent Number: 4,704,229
[45] Date of Patent: Nov. 3, 1987

[54] SURFACE-ACTIVE COMPOUNDS OF THE SULFOBETAINES FAMILY, THEIR MANUFACTURE AND USE, PARTICULARLY FOR ENHANCED OIL RECOVERY

[75] Inventors: Sylvain Brunel, Vienne; Laurent Germanaud, Irigny; Pierre Le Perchec; Bernard Sillion, both of Lyons, all of France

[73] Assignees: Institut Francais du Petrole, Rueil-Malmaison; Centre National de la Recherche Scientifique, Paris, both of France

[21] Appl. No.: 767,402

[22] Filed: Aug. 20, 1985

[30] Foreign Application Priority Data

Aug. 20, 1984 [FR] France .................. 84 13048

[51] Int. Cl.$^4$ .................. C07C 143/14; C07C 143/10; B01F 17/00; C09K 3/00
[52] U.S. Cl. .................. 252/352; 252/8.554; 252/545; 260/501.12
[58] Field of Search .................. 260/501.12; 252/352

[56] References Cited

U.S. PATENT DOCUMENTS

| | | | |
|---|---|---|---|
| 3,198,822 | 8/1965 | Mannheimer | 260/501.12 |
| 3,280,179 | 10/1966 | Ernst | 260/501.12 |
| 3,594,411 | 7/1971 | Kite et al. | 260/501.12 |
| 4,259,191 | 3/1981 | Wagner | 260/501.12 |
| 4,267,123 | 5/1981 | Chen et al. | 260/501.12 |
| 4,381,980 | 5/1983 | Ballschuh et al. | 260/501.12 |
| 4,383,929 | 5/1983 | Bertocchio et al. | 260/501.12 |

FOREIGN PATENT DOCUMENTS

| | | | |
|---|---|---|---|
| 1240872 | 5/1967 | Fed. Rep. of Germany | 260/501.12 |
| 7408653 | 12/1974 | Netherlands | 260/501.12 |

*Primary Examiner*—J. E. Evans
*Attorney, Agent, or Firm*—Millen & White

[57] ABSTRACT

New surface-active compounds of the sulfobetaines group are manufactured. They comply with the general formula:

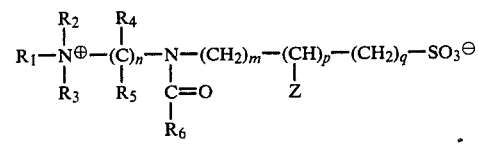

wherein each of $R_1$, $R_2$ and $R_3$ is substantially a hydrocarbon radical, each of $R_4$ and $R_5$ is a hydrogen atom or substantially a hydrocarbon radical and $R_6$ is a hydrogen atom or a hydrocarbon radical, $R_1$ to $R_6$ radicals containing together from 12 to 30 carbon atoms, n is an integer equal to 2 to 3, Z may be a $CH_3$ radical or a hydroxy group, p may be 0 or 1 with, when Z is a hydroxy group and p is equal to 1, a value of 1 for m and for q; when Z is a methyl radical, with a value of 1 for p, a value of 2 for m and a value of 0 or 1 for q and, when p=0, a value of 2, 3 or 4 for the sum (m+q).

These new surfactants are useful in enhanced oil recovery as micellar systems consisting of aqueous solutions and microemulsions.

20 Claims, No Drawings

SURFACE-ACTIVE COMPOUNDS OF THE SULFOBETAINES FAMILY, THEIR MANUFACTURE AND USE, PARTICULARLY FOR ENHANCED OIL RECOVERY

This invention relates to new surface-active compounds of the sulfobetaines group, to their manufacture and use.

BACKGROUND OF THE INVENTION

Surface-active agents of the sulfobetaines family are known to exhibit good complexing properties with respect to divalent ions and are hence of particular interest for hydrocarbons recovery by chemical techniques using micellar systems.

The object of enhanced oil recovery is to increase the oil recovery rate, on the one hand, by a more regular scavenging of the field and, on the other hand, by a sufficient reduction of the capillary forces, particularly by decreasing the interfacial tension between the oil and the injected fluid, thereby increasing the efficiency of the microscopic displacement.

The efficiency of scavenging by water injection is generally improved by reduction of the water mobility, achieved by adding hydrosoluble polymers thereto. Several processes have been proposed to increase the efficiency of the microscopic displacement of the injected fluid: injection of solvents (hydrocarbon gases, carbon dioxide, alcohols, liquefied petroleum gas, etc...), injection of alkaline water and solutions of surfactants in various forms: aqueous solutions, microemulsions, etc.... When using surfactants, usually in combination with hydrosoluble polymers, to stabilize the displacement, it appears that the recovery rate may reach 50% of the initial oil volume, and even, in favorable conditions, 70%.

A technique, now conventional, for decreasing the interfacial tension between the oil of the field and the injected fluid, consists of injecting a solution of surfactant whose characteristics are selected in relation with the conditions imposed by the field, particularly the water salt content, the nature of the oil in place and of the rock and the temperature. Then the injection of a hydrosoluble polymer solution is performed, followed with a water injection.

The surface-active compound is generally used at a concentration higher than the critical micellar concentration. The injected micellar systems are either aqueous solutions containing variable amounts of surfactants and, optionally, other additives such as co-surfactants, co-solvents, electrolytes, etc, or mixtures, in variable proportions, of water, electrolytes, hydrocarbons and, optionally, co-surfactants and/or co-solvents. In the latter case, the presence of polarapolar molecules at sufficient concentration leads to the formation of transparent mixtures, generally called microemulsions.

Many surfactant types have been proposed in the prior art for enhanced oil recovery. The most currently used surfactants, for reasons of cost and availability, are of the sulfonate type, more precisely petroleum sulfonates, as alkali metals or ammonium salts. The use of these surfactants is satisfactory as long as the water salt content does not exceed about 30 g/l (of sodium chloride equivalent) this value being given as order of magnitude: in particular, the interfacial tensions between oil and sulfonates solutions, obtained by a judicious selection of the product characteristics, are very low, about $10^{-3}$ mN/m, or even less. But, when the salt content substantially exceeds the above-mentioned value, it has been ascertained that the interfacial properties of sulfonates quickly degrade and the more as the content of divalent cations, calcium and magnesium particularly, is higher. Moreover, the high sensitivity of sulfonates to divalent cations produces, during the progress of the surfactant solution in the reservoir, precipitation and/or surfactant transfer phenomena in a stationary phase, which phenomena, associated with the release of cations by the rock, tend to make the surfactant inoperative.

It has been proposed to replace petroleum sulfonates with other types of anionic surfactants: for example paraffin-sulfonates, olefin-sulfonates, alkylsulfates, alkylphosphates, alkanoates, N acyl α-aminoalkanoates, carboxylates, sulfates and sulfonates of ethoxylated fatty alcohols and alkylphenols, etc... as well as non-ionic surfactants: for example ethoxylated fatty alcohols, ethoxylated alkylphenols, etc....

However, these surfactants, substitute of petroleum sulfonates, suffer from a high loss in their interfacial efficiency, when the salt content of the field water is high. Non-ionic surfactants are much less sensitive than anionic surfactants to the presence of divalent cations with respect to the risk of precipitation. On the contrary, their major defect results from the fact that their properties in solution (low interfacial tension in particular) are very sensitive to small temperature variations. Moreover, the distribution of this type of product (distribution in relation with the polydispersity) between the different liquid phases is such that it results in a decrease of its useful concentration in the solution. Finally, the cloud point appears at relatively low temperature.

The mixtures of anionic and non-ionic surfactants have been the object of many laboratory works and the results show that such mixtures exhibit interesting interfacial properties, even in the presence of divalent ions; however, when using them in porous medium, there is an obvious risk of selective physi- or chemisorption which would quickly change the composition of the mixture.

In view of the various disadvantages of the conventional surfactants, researches have been conducted on the use of other surface-active compounds and, more particularly, on compounds of the zwitterionic type, products whose surfactant properties are not affected, or only to a small extent, by the presence of polyvalent cations, and this within wide temperature and pH ranges.

The idea to fix on the same surfactant molecule two different hydrophilic parts has been developed in various laboratories working on the problems of enhanced recovery. For example, the behavior of oxyethylated alcohols, modified at the end of the hydrophilic chain by a sulfonic group introduced through various techniques, as well as products resulting from the modification of the oxyethylated alcohol with chloracetic acid, have been studied.

In the prior art, the sulfobetaine surfactants are obtained generally by condensation of a tertiary amine (one alkyl group of which contains from 10 to 25 carbon atoms) with a sultone, propane-sultone or butane-sultone, according to equation 1:

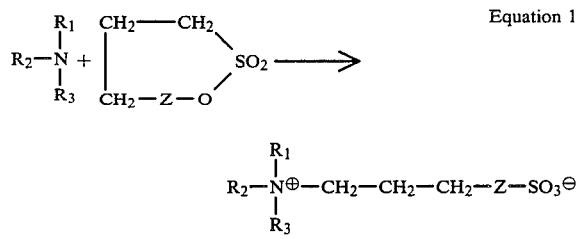

Equation 1 with $Z=(CH_2)_n$ and $n=0$ or 1.

The operation may also be conducted as described by R. G. Bristline, W. R. Noble and W. M. Linfield in J. Amer. Oil Chem. S. 53, 64, 1976 by reacting the same tertiary amines with the condensation product of epichlorhydrine on sodium bisulfite, according to equation 2:

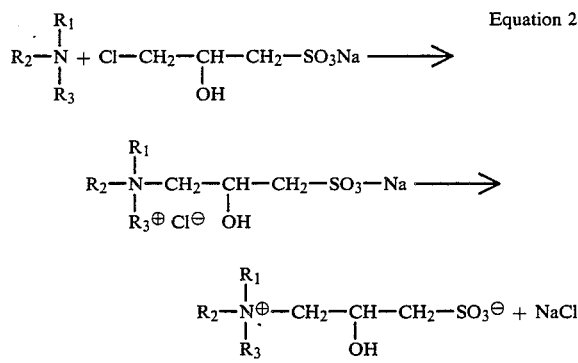

Equation 2

The resultant hydroxylated sulfobetaines have an improved solubility.

The same authors indicate that the quaternization of the tertiary amines by means of allyl chloride, followed with the addition of sodium sulfite, also leads to sulfobetaines according to equation 3:

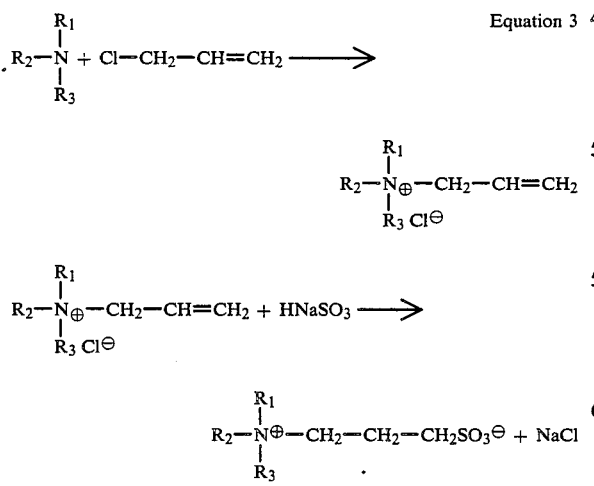

Equation 3

The condensation of ethylene sulfonic acid esters on tertiary amines salts have been disclosed, in the French Pat. No. 2 270 241, for manufacturing sulfobetaines according to equation 4:

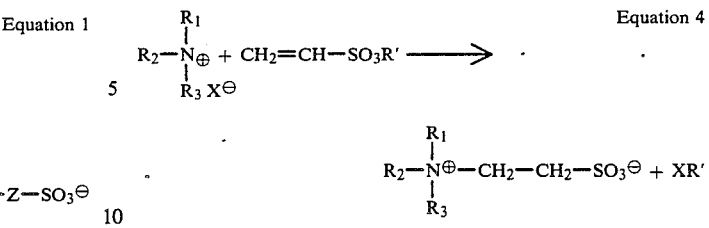

Equation 4

Moreover, it has been proposed to synthesize sulfobetaines of improved solubility by introducing hydrophilic groups such as amide groups. In this respect, U.S. Pat. No. 4,259,191 discloses products obtained by reacting propane-sultones with amides-amines derived from naphthenic acids, according to equation 5:

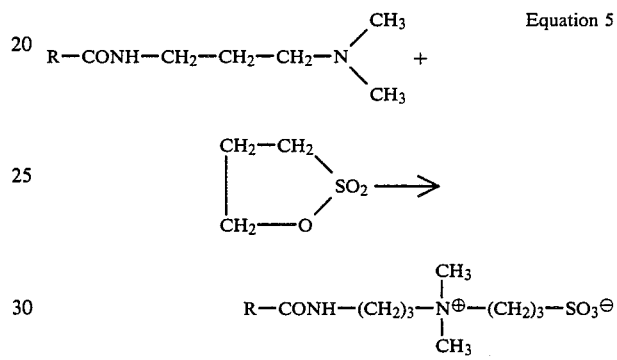

Equation 5 wherein R is a naphthenic acid remainder.

On the other hand, the surfactant properties of sulfobetaines and their excellent properties in hard waters have been mentioned and made obvious in several papers, such for example as the article of W. R. Noble and W. R. Linfield, J.A.O.C. 57, 368, 1980 and that of G. W. Fernley, J.A.O.C. 55, 98, 1978.

Their use in saline fields, containing in particular divalent ions, has been previously described. U.S. Pat. No. 4,216,097 discloses the use of a product complying with the formula:

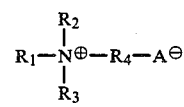

wherein $R_4$ contains from 1 to 6 carbon atoms and $A^\ominus$ is $COO^\ominus$ or $SO_3^\ominus$, $R_1$ being the lipophilic chain, but the longest $R_4$ chain in the mentioned compounds comprises a methylbutylene group. In this patent, interesting indications are given on the efficiency at low concentration of this type of products and on their low adsorption, and it is particularly mentioned that the use of the product $C_{16}H_{33}N^\oplus(CH_3)_2$—$CH_2$—$CH_2$—$SO_3^\ominus$ provides for an excellent recovery in a medium of high divalent ions concentration.

As a whole, in the sulfobetaines of the prior art, the distance between the two zwitterion poles is determined by the nature of the sulfonic reactant and this distance is generally limited to four carbon atoms in linear chain.

SUMMARY OF THE INVENTION

The present invention shows that it is possible to prepare sulfobetaines wherein the distance between the charges is higher than the distance inherent to the presence of four carbon atoms in linear chain, thus conferring them improved physical properties (e.g. solubility) and surfactant properties.

The sulfobetaines of the invention may be represented by the general formula:

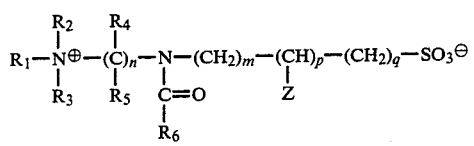
(I)

wherein each of $R_1$, $R_2$ and $R_3$ is substantially a hydrocarbon radical, each of $R_4$ and $R_5$, is a hydrogen atom or substantially a hydrocarbon radical and $R_6$ is a hydrogen atom or a hydrocarbon radical, $R_1$ to $R_6$ containing together from 12 to 30 carbon atoms, n is an integer equal to 2 or 3, Z may be a $CH_3$ radical or a hydroxy group, p may be 0 or 1 with, when Z is a hydroxy group and p is equal to 1, a value of 1 for m and for q; when Z is a methyl radical, and the value of p is 1, a value of 2 for m and a value of 0 or 1 for q and, when p=0, a value of 2, 3 or 4 for the sum (m+q).

The distance between the two zwitterion poles may thus be from 5 to 8 atoms in linear chain (carbon+nitrogen).

$R_1$, $R_2$ and $R_3$ are advantageously linear or branched aliphatic radicals, carrying or not hydroxy·groups, or aromatic or arylaliphatic radicals, one of the three radicals containing at least 10 carbon atoms, the two others containing 1 or 2 carbon atoms; $R_4$ and $R_5$ are advantageously hydrogen atoms, methyl or hydroxymethyl groups. They are preferably hydrogen atoms.

$R_6$ is advantageously a hydrogen atom or a linear or branched alkyl group containing 1 to 20 carbon atoms or an aryl group.

When the chain length results from all the groups $R_1$, $R_2$ and $R_3$, group $R_6$ will advantgeously contain from 1 to 6 carbon atoms and will be preferably a methyl group.

From the above-defined sulfobetaines the most interesting are those of formula (1) wherein $R_1$ is a $C_{12}$–$C_{18}$ linear saturated aliphatic radical, $R_2$ and $R_3$ are methyl radicals, $R_4$ and $R_5$ are both hydrogen atom, $R_6$ is a methyl radical, n is 2 or 3, p is 0 and (m+q) is 3 or 4.

The sulfobetaines according to the invention, complying with formula (I), are obtained in two main steps from cyclic iminoethers of the general formula:

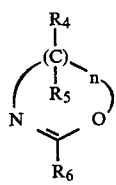
(II)

wherein $R_4$, $R_5$ and $R_6$ and n may have the values indicated for general formula (I).

Examples of cyclic iminoethers which can be used according to the invention are: 2-methyl, 2-oxazoline-1,3; 2-phenyl 2-oxazoline-1,3; 2-methyl 4,4-dimethyl 2-oxazoline-1,3; 2-methyl 5,5-dimethyl 2-oxazoline-1,3; 2-methyl 4-methyl 4-hydroxymethyl 2-oxazoline-1,3; 2-methyl 4,4-bishydroxymethyl 2-oxazoline-1,3; 2-hexyl 2-oxazoline-1,3; 2-nonyl 2-oxazoline-1,3; 2-methyl 5,6-dihydro 2-oxazine-1,3; 2-nonyl 5,6-dihydro 2-oxazine-1,3 and 2-phenyl 5,6-dihydro 2-oxazine-1,3.

Examples of sultones which can be used according to the invention are: propane sultone, butane sultone, 4-methyl butane sultone and 3-methyl propane sultone.

Cyclic iminoethers (II), used initially in the process for preparing products according to the invention, may be prepared by known methods comprising:

either the condensation of nitriles on 1,2 or 1,3-aminoalcohols, catalyzed by cadmium salts, as disclosed by W. Seeliger and coll., Angew. Chem. Intern. Ed. 5, (10), 875, 1966.

or the rearrangement of acylaziridine, for example according to the method described by A. I. Meyer and coll., J. Org. Chem. 39, (18) 2787, 1974.

In the first step, the cyclic iminoether (II) is converted to an intermediary sulfobetaine according to any one of the following methods: a first embodiment of this first step comprises condensing on the iminoether (II) a sultone of general formula:

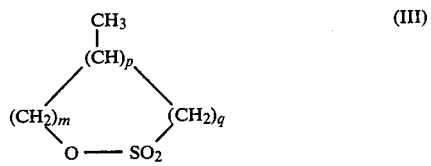
(III)

wherein, when p=0, (m+q) is 3 or 4 and, when p=1, m is 2 and q is 0 or 1, according to equation 6:

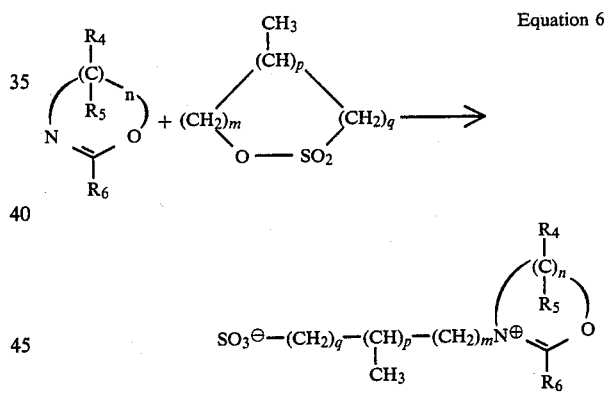
Equation 6 wherein m, p and q are defined as in formula (III).

The conditions of this reaction are generally as follows:

Preferably, the reactants are used in stoichiometrical proportions as a 10 to 30% molar solution in a chlorinated solvent, for example chlorobenzene. The reaction temperature may range from 20° to 70°C. The reaction time is from 1 hour to 24 hours.

The first step of the manufacturing process may also involve the reaction product of the sodium bisulfite with epichlorhydrine, which is condensed on the iminoether (II) according to equation 7.

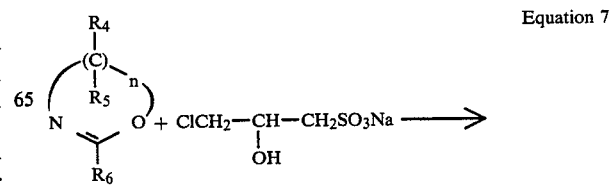
Equation 7

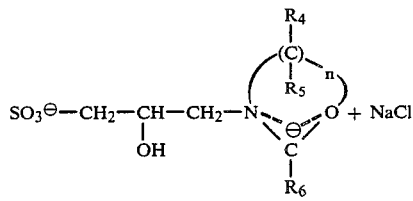    5

The reaction takes place in stoichiometrical conditions, in biphasic medium (water and hydrocarbon) at a temperature from 20° to 80° C.

The first step of the manufacturing process may also consist in the condensation of an ester of the ethylene sulfonic acid on an iminoether halohydrate or hydrogenosulfate of formula IIa, according to equation 8.

Equation 8

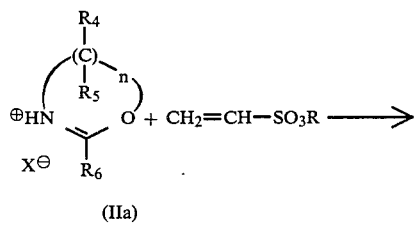

wherein R is an aliphatic radical containing 1 to 10 carbon atoms.

The manufacture of the products of equation 8 takes its inspiration from the papers of A. Le Berre, A. Etienne, A. Delacroix and A. Proust, Bull. Soc. Chem., 1975, no 11, page 2531 and Bull. Soc. Chem., 1973, no 7 page 2404.

According to another embodiment of the first step of the manufacturing process, the iminoether (II) may be condensed on the allylchloride and then the intermediary cyclic iminoether chloride is condensed on sodium bisulfite according to equation 9.

Equation 9

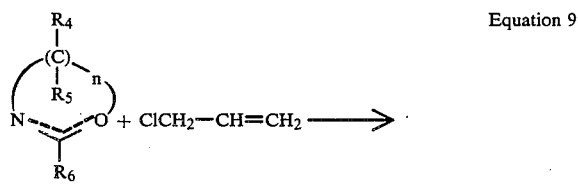

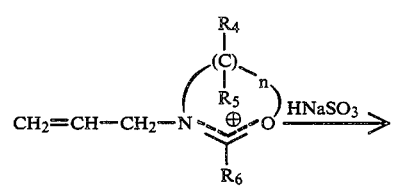

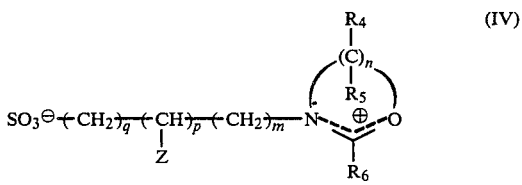

The first reaction takes place at room temperature in stoichiometrical conditions and in the presence of a hydrocarbon solvent, whereas the condensation on sodium bisulfite takes place in biphasic medium in stoichiometrical conditions and at a temperature from 20° to 80° C.

Any one of the above mentioned methods gives an intermediary sulfobetaine of general formula:

    (IV)

wherein $R_4$, $R_5$, Z, n, m, p, q and Z have the same meaning as above mentioned for the general formula I.

In the second step, the intermediary sulfobetaines (IV) are then condensed on tertiary amines of general formula:

$$R_1-\underset{\underset{R_3}{|}}{\overset{\overset{R_2}{|}}{N}} \quad (V)$$

wherein $R_1$, $R_2$, $R_3$ have the values indicated for formula (I); this condensation gives directly sulfobetaines (I) according to the invention.

Examples of amines which can be used according to the invention are: N,N-dimethyl octylamine, N,N-dimethyl decylamine, N,N-dimethyl dodecylamine, N,N-dimethyl octadecylamine, industrial mixtures resulting from methylation of fatty amines, of coprah and of tallow, N,N-bis(hydroxyethyl)dodecylamine and N,N-diethyl benzylamine.

The sulfobetaines according to the invention, as precedingly defined, may be advantageously used as surfactants in enhanced oil recovery.

The considered micellar systems may be defined generally by the fact that they contain, as surfactant, at least one sulfobetaine according to the invention, in admixture with water, optionally at least one hydrocarbon liquid, and optionally at least one cosurfactant. They can be used as pure products or as previously formed aqueous solutions, said solutions containing for example from 1 to 40% by weight of active material.

The micellar systems considered in the invention may consist of aqueous solutions at various concentrations of surfactants for example from 0.1 to 15% by weight.

These solutions may further contain at least one cosurfactant or a cosolvent such as hereinafter defined, in a proportion of, for example, up to 15% by weight with respect to the total weight of the solution.

The cosurfactants or "cosolvents" are mainly alcohols, particularly primary aliphatic mono-alcohols having 1 to 12 carbon atoms, and advantageously: n-propanol, isobutanol, n-1-butanol, n-1-pentanol, n-1-hexanol, n-1-heptanol, n-1-octanol, n-1-decanol or n-1-dodecanol or mixtures thereof.

Other cosurfactants which can be used are amines, acids, ethers, polyols, as well as non-ionic surfactants such as ethoxylates of fatty alcohols, of fatty acids or of alkylphenols, or still anionic surfactants such as compounds having sulfate, sulfonate, carboxylate or phosphonate groups. These various cosurfactants may be used alone or admixed with one another.

The surfactant and cosurfactant or the cosolvent may be used in different relative ratios; advantageously, the ratio by weight of the cosurfactant or the cosolvent to the surfactant will range from 0 to 5/1 and preferably from 1/1 to 3/1.

The water used to prepare these solutions, which may be optionally the field water, may contain mono and/or polyvalent cations, particularly $Na^+$, $K^+$, $Ca^{++}$ and $Mg^{++}$ (the total salt content being for example from 30 to 300 g/l). The water proportion ranges from 70 to 99.9%.

The micellar systems according to the invention may also consist of microemulsions comprising:

water, which, as above-mentioned, may contain mono and/or polyvalent cations, particularly $Na^+$, $K^+$, $Ca^{++}$ or $Mg^{++}$ (the total salt content being for example from 30 to 300 g/l);

at least one hydrocarbon liquid, which may be a pure hydrocarbon, containing for example from 8 to 16 carbon atoms, a mixture of hydrocarbons, an oil fractionation cut or even a crude oil;

at least one sulfobetaine as above-described; and optionally at least one co-surfactant (or cosolvent) as above-described.

The microemulsions may comprise various proportions of the different constituents, for example:

from 70 to 99.9% by weight of water and hydrocarbon liquid in a ratio by weight hydrocarbon liquid/water from 1/100 to 4/1 and preferably from 1/20 to 1/1, from 0.1 to 15% by weight of surfactant (sulfobetaine), from 0 to 15% by weight of cosurfactant.

EXAMPLES

The following examples illustrate the invention but must not be considered as limiting in any way the scope thereof.

EXAMPLE 1

Preparation of 3-(2-methyl 1,3-oxazolinium)propane sulfonate according to A. Forestiere and B. Sillion, J. Heterocyclic Chem. 17, 1381 (1980).

16 g (0,131 mole) of 1,3-propanesultone and 11.2 g (0.131 mole) of 2-methyl 1,3-oxazoline are reacted in 50 ml of chlorobenzene under stirring, at room temperature, in inert atmosphere. (Imperatively all the reactants must be freshly distilled). After 24 h, 50 ml of anhydrous cyclohexane are added, and the precipitated betaine crystals are centrifuged in inert gas, then washed with cyclohexane and dried under good vacuum. Thus, 23.6 g (87%) of very hygroscopic (F=236°) white crystals are obtained, which are identified by I.R. and proton N.M.R. spectrometry. The microanalysis corresponds to the theory.

EXAMPLE 2

Preparation of 4-acetyl-4-aza-6(N,N-dimethyl-laurylammonium)hexane sulfonate.

A mixture of 23.5 g (0.113 mole) of the betaine of example 1 and 33.8 ml (26.7 g; 0.125 mole) of distilled N,N-dimethyl laurylamine in 70 ml of anhydrous dimethyl formamide (DMF), is heated at 120° C. under stirring for 3 hours. The solvent is evaporated, taken again with 300 ml of permuted water, washed twice with 150 ml of chloroform (to remove the amine excess) and then concentrated to dryness. Three times 500 ml of dry methanol are added and evaporated and the product is dried under good vacuum. The obtained hygroscopic product is kept in argon. 40 g (89%) of product (vitrified oil) are obtained with a 95% purity, as ascertained by high performance liquid chromatography (HPLC). IR and $^1H$ NMR spectra confirm the structure and show that a few water remains; the results of microanalysis indicate the presence of 0.25 mole of water per mole of sulfobetaine.

EXAMPLE 3

Preparation of 4-acetyl-4-aza-6 (N,N-dimethyl stearylammonium) hexane sulfonate.

A mixture of 8.1 g (0.0391 mole) of the salt of example 1 and 12 g (0.0405 mole) of N,N-dimethylstearylamine in 40 ml of anhydrous DMF is heated at 120° C. for 3 hours, under stirring. The temperature is allowed to decrease to room temperature, said decrease being accompanied with the setting of the reaction medium, to which 100 ml of acetone must be added in order to separate crystals by centrifugation in inert gas, washing with acetone and drying. Thus 13 g (65%) of very hygroscopic white crystals are obtained, which are kept in argon. The structure is clearly determined by IR and $^1H$ NMR spectrometry and a sample recrystallized in an acetone-acetonitrile mixture (9/1 by volume) exhibits a micro-analysis in conformity with the raw formula.

EXAMPLE 4

Preparation of 3-(2-methyl 5,6-dihydro 1,3 oxazinium)-propane sulfonate.

9 g (0.09 mole) of 2-methyl 5,6-dihydro oxazine and 10.8 g (0.088 mole) of freshly distilled propane 1,3-sultone are reacted in solution in 35 ml of anhydrous chlorobenzene, under stirring at room temperature and in inert atmosphere. After 24 hours, 50 ml of dry cyclohexane are added and the crystals are centrifuged, washed with cyclohexane, then with acetone and dried under good vacuum. 16.35 g (84%) of very hygroscopic white crystals are obtained, as identified by $^1H$ NMR.

EXAMPLE 5

Preparation of 4-acetyl-4-aza-7 (N,N-dimethyl laurylammonium)heptane sulfonate.

A mixture of 16.3 g (0.074 mole) of betaine (ex. 4), with 22.5 ml (17.8 g; 0.083 mole) of N,N-dimethyl laurylamine (distilled) in 45 ml of anhydrous DMF is heated to 120° C. under stirring, an inert atmosphere, for 3 hours. The solvent is evaporated, taken again with 100 ml of permuted water, washed with 2×50 ml of chloroform (removal of residual amine) and then 3×250 ml of dry methanol are added thereto and evaporated and the resultant product is dried under good vacuum. There is so obtained 30.7 g (93%) of a hygroscopic solid product (vitrified oil) which is kept in argon.

The structure is ascertained by IR and $^1$H NMR spectrometry showing the presence of water. The purity, as determined by HPLC, is 100% and the microanalysis gives results in agreement with the structure, the presence of 0.75 mole of water per mole of sulfobetaine being taken into account.

EXAMPLE 6

Preparation of 4-(2-methyl 5,6-dihydro 1,3-oxazinium)-butane sulfonate.

A mixture of 13.6 g (0.1 mole) of butane 1,4 sultone and 10 g (0.1 mole) of 2-methyl-5,6 dihydro oxazine in 50 ml of anhydrous chlorobenzene is heated at 70° C., under stirring, in inert atmosphere, for 24 hours. After cooling, two turbid liquid phases are obtained. The supernatant phase is removed and dry acetone is added to crystallize the product. After centrifugation, washing with acetone and drying, a very hygroscopic paste is obtained (12 g; 51%) whose structure is confirmed by proton NMR.

EXAMPLE 7

Preparation of 5-acetyl-5-aza-8 (N,N-dimethyl-stearylammonium)octane sulfonate.

A mixture of the product obtained in example 6 (0.05 mole) with 16.3 g (0.055 mole) of N,N-dimethylstearylamine in 40 ml of anhydrous DMF is stirred in inert gas for 24 hours at 120° C.

A part of the DMF is evaporated under good vacuum, anhydrous acetone is added, the product is filtered in inert atmosphere and dried under good vacuum. Thus, 15.8 g (59%) of beige crystals are obtained. They are recrystallized in an acetonemethanol mixture (99/1 volume) to obtain 15.5 g (58%) of white crystals characterized by IR and $^1$H NMR spectrometry (presence of water). The micro-analysis is correct when taking into account the presence of 0.25 mole of water per mole of sulfobetaine.

EXAMPLE 8

Solubility in water at 20° C. of the sulfobetaines of examples 2, 3, 5 and 7 (Table I).

TABLE I

| FORMULA | Example | Solubility (g/l) |
|---|---|---|
| $SO_3^\ominus$-(CH$_2$)$_3$-N$^\oplus$(CH$_3$)-(CH$_2$)$_2$-N(COCH$_3$)-lauryl | 2 | 300 |
| $SO_3^\ominus$-(CH$_2$)$_3$-N$^\oplus$(CH$_3$)-(CH$_2$)$_2$-N(COCH$_3$)-stearyl | 3 | 80 |
| $SO_3^\ominus$-(CH$_2$)$_3$-N$^\oplus$(CH$_3$)-(CH$_2$)$_3$-N(COCH$_3$)-lauryl | 5 | 300 |
| $SO_3^\ominus$-(CH$_2$)$_4$-N$^\oplus$(CH$_3$)-(CH$_2$)$_3$-N(COCH$_3$)-stearyl | 7 | 4 |

EXAMPLE 9

Measurement of the critical micellar concentration (CMC) of the sulfobetaines of examples 2, 3, 5, and 7.

The critical micellar concentration of an amphiphilic compound is defined as the minimum concentration below which the micelle concentration becomes nil as well as the properties depending thereon (refraction index, density, specific conductivity, turbidity, osmotic coefficient, surface tension and solubility of a solvent insoluble in water) according to R. J. Williams et al., Trans. Farady Soc. 1968.

Preparation of solutions for the measurements of CMC values.

The method is a standard method using solutions of initial surfactant (SA) concentration of 0.5 g/l, in freshly permuted water, at room temperature of 20° C. The SA-water mixture is stirred up to complete dissolution and then a series of titrated solutions are obtained by successive dilution, by withdrawing a determined volume of mother-solution, brought each time to a standard volume i.e. 1 ml+39 ml; 2 ml+38 ml; 3 ml+37 ml; ... The various solutions are stirred for 30 minutes and maintained at rest for 2 hours. The surface tensions are measured by means of a tensiometer Tensiomat n$^3$ Prolabo whose operating principle consists of measuring the pullout load of a stirrup piece placed at the water/SA-ambient air interface, expressed in millinewton/meter.

The CMC value corresponds to the inflection point of the obtained two straight lines.

The values are summarized in Table II.

TABLE II

| FORMULA | EXAMPLE | CMC (g/l) | Surface tension (mN/m) |
|---|---|---|---|
| $SO_3^\ominus$-(CH$_2$)$_3$-N$^\oplus$(CH$_3$)-(CH$_2$)$_2$-N(COCH$_3$)-lauryl | 2 | 0.04 | 54 |
| $SO_3^\ominus$-(CH$_2$)$_3$-N$^\oplus$(CH$_3$)-(CH$_2$)$_2$-N(COCH$_3$)-stearyl | 3 | 0.01 | 35 |
| $SO_3^\ominus$-(CH$_2$)$_3$-N$^\oplus$(CH$_3$)-(CH$_2$)$_3$-N(COCH$_3$)-lauryl | 5 | 0.15 | 49 |

TABLE II-continued

| FORMULA | EXAMPLE | CMC (g/l) | Surface tension (mN/m) |
|---|---|---|---|
| 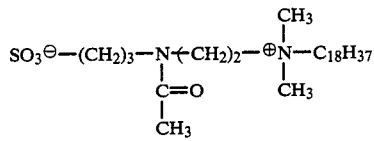 | 7 | 0.0028 | 39 |

EXAMPLE 10

Micro-emulsion test: Determination of optimum solubility and optimum salt content parameters.

The surface-active properties have been determined by analysis of the behaviour of sulfobetaines in a mixture defined according to standard conditions:
brine (NaCl, $CaCl_2$ with (NaCl/$CaCl_2$)=(9/1): 4.5 g
surfactant: 500 mg
cosurfactant: 500 mg
oil: 4.5 g.

Depending on the salt content of the brine (0–200 g/l), three mono-, di- or triphasic systems can be observed when the product has surface-active properties:
(1) the behavior referred to as Windsor I, wherein an equilibrium is observed between oil phase and $\mu\epsilon$ phase*.
(2) a behavior referred to as Windsor II, wherein an equilibrium is observed between $\mu\epsilon$ phase and aqueous phase.
(3) and, finally, a so-called Windsor III systems, wherein the intermediary $\mu\epsilon$ phase is in equilibrium with a supernatant oil phase and an aqueous phase.
*microemulsion The latter system has the pecularity of very low interfacial tensions. In this connection, it is efficient and hence useful for untrapping droplets retained by capillary forces. The optimum solubility and optimum salinity parameters, corresponding to equal amounts of water and oil in the micro-emulsion, are defined in this system.

By way of example, for sulfobetaine:

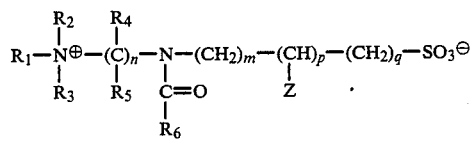

the following parameters have been obtained with pentanol as cosurfactant and dodecane as oil:
optimum salinity parameter: 30 g/l,
optimum solubility parameter: 55%.

What is claimed as the invention is:

1. A sulfobetaine characterized by the general formula $$R_1-\overset{R_2}{\underset{R_3}{N^{\oplus}}}-(C)_n\overset{R_4}{\underset{R_5}{|}}-N-(CH_2)_m-(CH)_p-(CH_2)_q-SO_3^{\ominus} \quad (I)$$

with $C=O$ and $R_6$ attached, and $Z$ on the CH.

wherein each of $R_1$, $R_2$ and $R_3$ is an unsubstituted hydrocarbon radical or a hydroxy substituted hydrocarbon radical, each of $R_4$ and $R_5$ is a hydrogen atom, an unsubstituted hydrocarbon radical, or a hydroxy substituted hydrocarbon radical and $R_6$ is a hydrogen atom or a hydrocarbon radical, $R_1$ to $R_6$ radicals containing together from 12 to 30 carbon atoms, n is an integer equal to 2 or 3, Z may be a $CH_3$ radical or a hydroxy group, p may be 0 or 1 with, when Z is a hydroxy group and p is equal to 1, a value of 1 for m and for Q; when Z is a methyl radical, and the value of p is 1, a value of 2 for m and a value of 0 or 1 for q and, when p=0, a value of 2, 3 or 4 for the sum (m+q).

2. A sulfobetaine according to claim 1, characterized in that $R_1$, $R_2$ and $R_3$ are linear or branched aliphatic radicals, carrying or not hydroxy groups, or aromatic or arylaliphatic radicals, one of the three radicals containing at least 10 carbon atoms, the two others containing 1 or 2 carbon atoms.

3. A sulfobetaine according to claim 1, characterized in that $R_4$ and $R_5$ are hydrogen atoms, methyl or hydroxymethyl groups and $R_6$ is a hydrogen atom, a linear or branched alkyl group containing 1 to 20 carbon atoms or an aryl group.

4. A sulfobetaine according to claim 2, characterized in that $R_6$ is an alkyl radical of 1 to 6 carbon atoms.

5. A sulfobetaine according to claim 1, characterized in that $R_1$ is a $C_{12}$–$C_{18}$ linear saturated aliphatic radical, $R_2$ and $R_3$ are methyl radicals, n is 2 or 3, p is 0 and (m+q) is equal to 3 or 4.

6. A composition characterized in that it contains as surfactant, a sulfobetaine according to claim 1, in admixture with water.

7. A composition according to claim 6, containing: from 0.1 to 15% by weight of sulfobetaine.

8. A composition according to claim 6 characterized in that the water has a total salt content from 30 to 300 g/l.

9. A composition characterized in that it contains, as surfactant, a sulfobetaine according to claim 2, in admixture with water.

10. A composition characterized in that it contains, as surfactant, a sulfobetaine according to claim 3, in admixture with water.

11. A composition characterized in that it contains, as surfactant, a sulfobetaine according to claim 4, in admixture with water.

12. A composition characterized in that it contains, as surfactant, a sulfobetaine according to claim 5, in admixture with water.

13. A composition according to claim 9, containing from 0.1 to 15% by weight of sulfobetaine.

14. A composition according to claim 12, containing from 0.1 to 15% by weight of sulfobetaine.

15. A composition according to claim 12 characterized in that the water has a total salt content from 30 to 300 g/l.

16. A composition according to claim 10, containing: from 0.1 to 15% by weight of sulfobetaine.

17. A composition according to claim 11, containing: from 0.1 to 15% by weight of sulfobetaine.

18. A composition according to claim 9 characterized in that the water has a total salt content from 30 to 300 g/l.

19. A composition according to claim 10 characterized in that the water has a total salt content from 30 to 300 g/l.

20. A composition according to claim 11, characterized in that the water has a total salt content from 30 to 300 g/l.

* * * * *